United States Patent
Rodrigues

(10) Patent No.: US 11,542,187 B2
(45) Date of Patent: Jan. 3, 2023

(54) COMPOSITION AND METHOD FOR CONTROLLING SCALE IN INDUSTRIAL WATER SYSTEMS

(71) Applicant: NOURYON CHEMICALS INTERNATIONAL B.V., Arnhem (NL)

(72) Inventor: Klin Aloysius Rodrigues, Signal Mountain, TN (US)

(73) Assignee: NOURYON CHEMICALS INTERNATIONAL B.V., Arnhem (NL)

( * ) Notice: Subject to any disclaimer, the term of this patent is extended or adjusted under 35 U.S.C. 154(b) by 271 days.

(21) Appl. No.: 16/751,456

(22) Filed: Jan. 24, 2020

(65) Prior Publication Data

US 2020/0239344 A1    Jul. 30, 2020

Related U.S. Application Data

(60) Provisional application No. 62/796,947, filed on Jan. 25, 2019.

(30) Foreign Application Priority Data

Mar. 14, 2019 (EP) .................... 19162897

(51) Int. Cl.

| | |
|---|---|
| C02F 5/12 | (2006.01) |
| C02F 5/14 | (2006.01) |
| C08F 12/32 | (2006.01) |
| C08F 28/02 | (2006.01) |
| C08F 30/02 | (2006.01) |
| C08F 228/02 | (2006.01) |
| C08F 230/02 | (2006.01) |
| C02F 103/02 | (2006.01) |
| C07C 309/72 | (2006.01) |
| C09K 11/06 | (2006.01) |
| C07C 15/38 | (2006.01) |

(52) U.S. Cl.
CPC .............. *C02F 5/12* (2013.01); *C02F 5/14* (2013.01); *C08F 12/32* (2013.01); *C08F 28/02* (2013.01); *C08F 30/02* (2013.01); *C08F 228/02* (2013.01); *C08F 230/02* (2013.01); *C02F 2103/023* (2013.01); *C07C 15/38* (2013.01); *C07C 309/72* (2013.01); *C09K 11/06* (2013.01)

(58) Field of Classification Search
None
See application file for complete search history.

(56) References Cited

U.S. PATENT DOCUMENTS

| 5,171,450 A | 12/1992 | Hoots |
|---|---|---|
| 5,986,030 A | 11/1999 | Murray et al. |
| 6,280,635 B1 | 8/2001 | Moriarty et al. |
| 6,312,644 B1 * | 11/2001 | Moriarty ............... C09K 11/06 |
| | | 252/180 |
| 2005/0244315 A1 | 11/2005 | Greaves et al. |
| 2016/0229726 A1 * | 8/2016 | Felipe .................. C23F 11/167 |

FOREIGN PATENT DOCUMENTS

| WO | 01/44403 A1 | 6/2001 |
|---|---|---|
| WO | 2019/025305 A1 | 2/2019 |

* cited by examiner

*Primary Examiner* — Clare M Perrin
(74) *Attorney, Agent, or Firm* — Norris McLaughlin, P.A.

(57) ABSTRACT

A fluorescent water treatment polymer comprises at least one water soluble carboxylic acid monomer other than maleic acid, at least one sulfonated pyrene-containing fluorescent monomer, and at least one phosphino group wherein the phosphorous atom of the phosphino group is in the polymer backbone. Additional monomers can be present, with the proviso that if maleic acid is present it comprises no greater than 75 mol % of the polymer. Surprisingly, it has been found that when the phosphino group is present the polymers exhibit an unexpectedly strong fluorescent signal strength. The signal strength of the fluorescent monomer in the polymer is further enhanced when the polymer comprises no greater than 75 mol % maleic acid.

15 Claims, No Drawings

COMPOSITION AND METHOD FOR CONTROLLING SCALE IN INDUSTRIAL WATER SYSTEMS

PRIORITY CLAIM

This application claims priority of European Patent Application No. 19162897.3, filed Mar. 14, 2019, and U.S. Provisional Application Ser. No. 62/796,947, filed Jan. 25, 2019, the contents of which applications are hereby incorporated herein by reference.

FIELD OF THE INVENTION

This application relates to a composition and method for controlling scale in industrial water systems by treatment with a fluorescent water treatment polymer containing a sulfonated pyrene monomer. More particularly, this application relates to a such a composition and method for controlling scale in industrial water systems by treatment with a fluorescent water treatment polymer containing a sulfonated pyrene monomer and that has a detectable fluorescent signal.

BACKGROUND

There are many industrial water systems, including, but not limited to, cooling water systems and boiler water systems. Such industrial water systems are subject to corrosion and the formation of scale.

It is known that certain types of water soluble treatment polymers are effective for preventing formation of scale and suppressing the occurrence of corrosion in industrial water systems. These water soluble treatment polymers are known to persons of ordinary skill in the art of industrial water systems and are widely used in scale inhibition products. Such water soluble treatment polymers generally exhibit activity against scale when added to water in an amount in the range of from about 1 to about 100 ppm.

The efficacy of water soluble treatment polymers in inhibiting scale and suppressing corrosion depends in part on the concentration of the water soluble treatment polymer in the water system. Water soluble treatment polymers added to an industrial water system can be consumed by many causes, leading to changes in concentration of the water soluble treatment polymer. Therefore, it is important for the optimum operation of an industrial water system to be able to accurately determine the concentration of water soluble treatment polymers in the water.

It is known that the concentration of water soluble treatment polymers used as components of scale and corrosion inhibitors in industrial water systems can be monitored if the polymer is tagged with a fluorescent monomer. The amount of fluorescent monomer incorporated into the water soluble polymer must be enough so that the fluorescence of the water soluble polymer can be adequately measured, however, it must not be so much as to adversely impact the performance of the water soluble polymer as a treatment agent. Because the concentration of the tagged water soluble treatment polymer can be determined using a fluorimeter, it is also possible to measure consumption of the water soluble treatment polymer directly. It is important to be able to measure consumption directly because consumption of a water soluble treatment polymer usually indicates that a non-desired event, such as scaling, is occurring. Thus by being able to measure consumption of the water soluble treatment polymer, there can be achieved an in-line, real time in situ measurement of scaling activity in the industrial water system. Such in-line, real time measurement systems are disclosed, for example, in U.S. Pat. Nos. 5,171,450, 5,986,030, and 6,280,635, all of which are incorporated herein by reference. The sulfonated pyrene compound known as pyranine is a known fluorescent compound that can be converted to a polymerizable fluorescent monomer for use in such systems. Other polymerizable fluorescent monomers are known in the art.

A wide array of water treatment formulations will also contain phosphate to minimize corrosion. Many states now have regulations limiting the amount of phosphates that can be used in water treatment systems or otherwise be potentially released to the environment. Even in states where the use of phosphate is allowed, it is considered desirable to minimize the amount of phosphate released to the environment. Therefore, the use of higher pH water systems that are lower in phosphates is becoming more common. But such higher pH water systems lead to increased carbonate scaling. Therefore, there is a need for methods of controlling carbonate scale in industrial water systems, particularly in higher pH environments.

It is further known in the art that some water soluble treatment polymers will be more effective in the treatment of phosphate scale, while other water soluble treatment polymers will be more effective in the treatment of carbonate scale. Homopolymers of maleic acid and copolymers of acrylic and maleic acids are conventionally used as carbonate scale control agents in water treatment applications. When tagged with a small amount of fluorescent sulfonated pyrene-containing monomer, such maleic homopolymers and high-maleic copolymers typically exhibit poor to very low fluorescent signal strength.

It thus would be desirable to provide compositions and methods for controlling scale in industrial water systems comprising a sulfonated pyrene-containing fluorescent water treatment polymer that provides a detectable fluorescent signal under typical industrial water treatment conditions.

SUMMARY OF THE DISCLOSURE

This application is based on the surprising discovery that certain fluorescent sulfonated pyrene-containing monomers exhibit unexpectedly strong signal strength when present in water treatment polymers wherein the polymer backbone comprises phosphino groups.

In one aspect of the disclosure, a fluorescent water treatment polymer comprises
  (i) at least one water soluble carboxylic acid monomer, other than maleic acid, present in an amount of 10-99.998 mol %;
  (ii) at least one sulfonated pyrene-containing fluorescent monomer as disclosed hereinbelow, said sulfonated pyrene-containing fluorescent monomer being present in an amount of 0.001-5 mol %; and
  (iii) at least one phosphino group wherein the phosphorous atom of the phosphino group is in the polymer backbone, said phosphino group being present in an amount of 0.001-20 mol %.

In one aspect, the fluorescent water treatment polymer may also include additional monomers, including but not limited to phosphono groups, phosphate-containing monomers, sulfonic containing monomers, other nonionic monomers, and maleic acid, with the proviso that if maleic is present it comprises no greater than 75 mol % of the fluorescent water treatment polymer.

In one aspect of the disclosure, a water treatment formulation for use in controlling scale in an industrial water system comprises a fluorescent water treatment polymer as described above.

In one aspect of the disclosure, a method of controlling scale in an industrial water system comprises the steps of
(a) dosing the water system with a fluorescent water treatment polymer for controlling scale as described above; and
(b) monitoring the fluorescent emissions of the dosed water system.

In one embodiment, the fluorescent water treatment polymer is free of polyether moieties.

Surprisingly, it has been found that when a phosphino group is present in the backbone of the sulfonated pyrene-containing fluorescent water treatment polymer, there is an unexpected boost in fluorescent signal strength of the sulfonated pyrene fluorescent monomer in the polymer. The fluorescent signal strength is further enhanced when the water treatment polymer comprises no more than 75 mol % maleic acid.

DETAILED DESCRIPTION

For purposes of this application, the term "maleic component" shall mean, with respect to a polymerization mixture used to make a water treatment polymer, a monomer that is substituted or unsubstituted polymerizable maleic acid or maleic anhydride.

For purposes of this application, the term "mole percent" of a monomer or polymerizable moiety in a polymer shall mean the mole fraction of the monomer or polymerizable moiety with respect to the total moles of monomers and polymerizable moieties included in the polymerization reaction mixture from which the polymer is obtained.

As used herein, the term "(meth)acrylic" acid is meant to include both acrylic acid and methacrylic acid. Similarly, the term "alkyl (meth)acrylate" as used herein is meant to include alkyl acrylate and alkyl methacrylate.

For purposes of this application, the term "scale" includes carbonate scale, sulfate scale, silica and silicate scale and phosphate scale, except where indicated otherwise. Carbonate scale includes calcium carbonate scale and/or magnesium carbonate scale.

Disclosed herein is a fluorescent water treatment polymer comprising
(i) at least one water soluble carboxylic acid monomer, other than maleic acid, present in an amount of 10-99.998 mol %;
(ii) at least one sulfonated pyrene-containing fluorescent monomer selected from

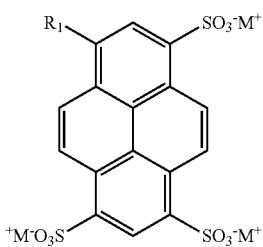

Structure (I)

wherein $R_1$ is selected from the group consisting of (meth)allyloxy, vinyl benzyloxy, (meth)acryl, (meth)acrylamidopropyl, 2-hydroxy-3-(meth)allyloxypropyl, (meth)acrylamido, 3-isopropenyl-α,α-dimethylbenzyl urethane, and (meth)allyl urethane,
and $M^+$ is independently selected from hydrogen, alkali metal, alkaline earth metal, and amine salt,
and

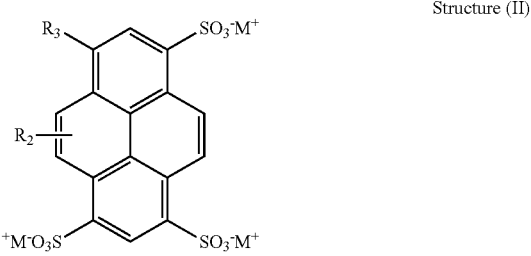

Structure (II)

wherein $R_2$ is selected from the group consisting of (meth)allyl, vinyl benzyl, (meth)acryl, (meth)acrylamidopropyl, and 2-hydroxy-3-(meth)allyloxypropyl,
$R_3$ is selected from hydrogen, —OH, and —$SO_3$-$M^+$, and
$M^+$ is independently selected from hydrogen, alkali metal, alkaline earth metal, and amine salt,
said sulfonated pyrene-containing fluorescent monomer being present in an amount of 0.001-5 mol %; and
(iii) at least one phosphino group wherein the phosphorous atom of the phosphino group is in the polymer backbone, said phosphino group being present in an amount of 0.001-20 mol %.

In one aspect, the fluorescent water treatment polymer may also include additional monomers, including but not limited to phosphono groups, phosphate-containing monomers, sulfonic containing monomers, other nonionic monomers, and maleic acid, with the proviso that if maleic acid is present it comprises no greater than 75 mol % of the fluorescent water treatment polymer.

In one aspect, maleic acid comprises no greater than 60 mol % of the fluorescent water treatment polymer, in one aspect no greater than 30 mol % of the fluorescent water treatment polymer, in one aspect no greater than 10 mol % of the fluorescent water treatment polymer, in one aspect no greater than 5 mol % of the fluorescent water treatment polymer, in one aspect no greater than 1 mol % of the fluorescent water treatment polymer. In one aspect, the water treatment polymer is free of maleic acid.

In one embodiment, the fluorescent water treatment polymer comprises polyether moieties.

In one embodiment, the fluorescent water treatment polymer is free of polyether moieties.

In one aspect of the disclosure, a water treatment formulation for use in controlling scale in an industrial water system comprises a fluorescent water treatment polymer as described above.

Also disclosed herein is a method of controlling scale in an industrial water system, the method comprising the steps of
(a) dosing the water system with a fluorescent water treatment polymer as described above,
and
(b) monitoring the fluorescent emissions of the dosed water system.

Surprisingly, it has been found that when phosphino groups are present in the water treatment polymer backbone, there is an unexpected boost in fluorescent signal strength of the sulfonated pyrene fluorescent monomer in the polymer. The signal strength can be further enhanced when the maleic component of the sulfonated pyrene-containing fluorescent water treatment polymer is no greater than 75 mol %. Thus the disclosed fluorescent water treatment polymers, formulations thereof and methods of controlling scale allow for the use of water treatment polymers having a smaller percentage of the sulfonated pyrene-containing fluorescent monomer than was previously believed necessary for the polymer to be detected by fluorimetry, and also may allow for use of less of the water treatment polymer itself. In one embodiment, for a water system having a Langelier Saturation Index (LSI) of 2, carbonate inhibition of at least 80% is achieved when the water treatment polymer in accordance with the disclosed method is dosed to a water system at no greater than 100 ppm, more preferably carbonate inhibition of at least 80% is achieved when the water treatment polymer in accordance with the disclosed method is dosed to a water system at no greater than 50 ppm, and most preferably carbonate inhibition of at least 90% is achieved when the water treatment polymer in accordance with the disclosed method is dosed to a water system at no greater than 20 ppm. The disclosed method of controlling carbonate scale also will be effective in water treatment systems having LSI values less than or greater than 2.

(i) Carboxylic Acid Monomers Other than Maleic Acid or Maleic Anhydride

For purposes of this application, the at least one water soluble carboxylic acid monomer other than maleic acid can be a monocarboxylic acid monomer or dicarboxylic acidic monomer. Such carboxylic acid monomers can be selected from one or more of the group consisting of acrylic acid, methacrylic acid, itaconic acid, citraconic acid, mesaconic acid, glutaconic acid, aconitic acid, ethacrylic acid, alpha-chloro-acrylic acid, alpha-cyano acrylic acid, alpha-chloro-methacrylic acid, alpha-cyano methacrylic acid, beta methyl-acrylic acid (crotonic acid), beta-acryloxy propionic acid, sorbic acid, alpha-chloro sorbic acid, angelic acid, tiglic acid, p-chloro cinnamic acid, monomethyl maleate, monoethyl maleate, salts and anhydrides of any of the foregoing, and mixtures of any of the foregoing. In one embodiment, the at least one water soluble carboxylic acid monomer is selected from one or more of acrylic acid, methacrylic acid and itaconic acid, and their salts and anhydrides, and mixtures of any of the foregoing. In one embodiment, the at least one water-soluble carboxylic acid monomer is selected from acrylic acid and methacrylic acid and their salts and anhydrides and mixtures thereof. In one embodiment, the at least one water-soluble carboxylic acid monomer is acrylic acid.

As used herein with respect to water soluble carboxylic acid monomers, water soluble means that the monomer has a water solubility as the acid of greater than 1 gram per 100 mls of water at 25° C., preferably greater than 3 grams per 100 mls of water at 25° C., and most preferably greater than 6 grams per 100 mls of water at 25° C.

The water soluble carboxylic acid monomers will be present in the polymerization mixture in the range of 10-99.998 mol %, in one embodiment in the range of 30-99.998 mol %, in one embodiment in the range of 40-99.998 mol %, in one embodiment in the range of 50-99.998 mol %, in one embodiment in the range of 70-99.998 mol %, in one embodiment in the range of 90-99.998 mol %.

(ii) Fluorescent Monomers

Fluorescent monomers include without limitation one or more polymerizable derivatives of sulfonated pyrene of Structure (I) or Structure (II).

In one embodiment the fluorescent monomer is

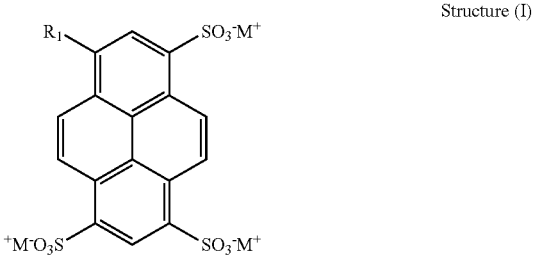

Structure (I)

wherein $R_1$ is selected from the group consisting of (meth)allyloxy, vinyl benzyloxy, (meth)acryl, (meth)acrylamidopropyl, 2-hydroxy-3-(meth)allyloxypropyl, (meth)acrylamido, 3-isopropenyl-α,α-dimethylbenzyl urethane, and (meth)allyl urethane, and $M^+$ is independently selected from hydrogen, alkali metal, alkaline earth metal, and amine salt.

In one embodiment the fluorescent monomer is

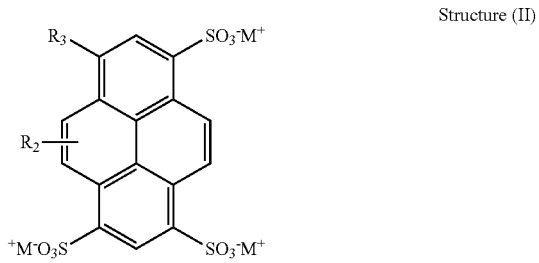

Structure (II)

where $R_2$ is selected from the group consisting of (meth)allyl, vinyl benzyl, (meth)acryl, (meth)acrylamidopropyl, and 2-hydroxy-3-(meth)allyloxypropyl;

$R_3$ is selected from hydrogen, —OH, or —$SO_3^-M^+$; and $M^+$ is independently selected from hydrogen, alkali metal, alkaline earth metal and amine salt.

In one embodiment the fluorescent monomer can be a mixture of monomers of Structure (I) and Structure (II).

Advantageously, the fluorescence of the selected monomer in the fluorescent water treatment polymer will not be inhibited or suppressed by the presence of calcium or magnesium or other ions that contribute to hardness of the water in the water system. In one embodiment, the fluorescent signal of the fluorescent water treatment polymer drops less than 10% in the presence of 100 ppm of calcium as calcium carbonate, more preferably the fluorescent signal drops less than 10% in the presence of 500 ppm of calcium as calcium carbonate, and most preferably the fluorescent signal drops less than 10% in the presence of 1000 ppm of calcium as calcium carbonate.

The sulfonated pyrene containing fluorescent monomer is present in the fluorescent water treatment polymer in an amount of 0.001-1 mol %. In one aspect the fluorescent monomer is present in the polymerization mixture as no greater than 0.5 mol %, in still another aspect no greater than 0.25 mol %. In one aspect the fluorescent monomer will be present in the water treatment polymer as at least 0.001 mol %, in another aspect at least 0.005 mol %, in another aspect at least 0.01 mol %, in another aspect at least 0.05 mol %, in another aspect as at least 0.10 mol %.

(iii) Phosphino Groups

At least one phosphino group is present wherein the phosphorous atom of the phosphino group is in the polymer backbone. The term "in the backbone" as used herein includes moieties of the structure

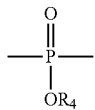

where the group is between other monomers of the backbone of the polymer, and moieties of the structure

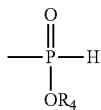

where the group is an end group in the polymer.

Phosphinic acid or phosphinate groups may be incorporated in the water treatment polymer backbone as phosphino groups by including in the polymerization mixture molecules of Structure (III)

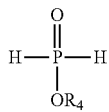

Structure (III)

where $R_4$ is selected from hydrogen, $C_1$-$C_4$ alkyl, phenyl, alkali metal, alkaline earth metal, an ammonium ion and an amine residue. These molecules of Structure (III) which can incorporate phosphinic or phosphinate groups into the water treatment polymer backbone include but are not limited to hypophosphorous acid and its salts, such as sodium hypophosphite.

The at least one phosphino group is present in the water treatment polymer in the range of no greater than 20 mol %; in another aspect no greater than 10 mol %, in still another aspect no greater than 5 mol %, in still another aspect no greater than 3 mol %, in another aspect no greater than 1 mol %.

Optional Additional Monomers

Maleic Acid

Although commonly used in water treatment polymers, it has been found that maleic acid suppresses the signal strength of the sulfonated pyrene fluorescent monomers. Accordingly, maleic acid if present comprises no greater than 75 mol % of the fluorescent water treatment polymer.

Phosphorous Containing Monomers

Phosphonic acid or phosphonate groups may be incorporated as phosphono end groups of the water treatment polymer by including in the polymerization mixture molecules of Structure (IV)

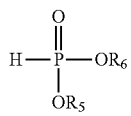

Structure (IV)

where $R_5$ and $R_6$ are independently selected from hydrogen, $C_1$-$C_4$ alkyl, phenyl, alkali metal, alkaline earth metal, ammonium ion or an amine residue. These structures include but are not limited to orthophosphorous acid and its salts and derivatives such as dimethyl phosphite, diethyl phosphite and diphenyl phosphite.

Phosphonate groups that are pendant from the water treatment polymer backbone may be incorporated by including in the polymerization mixture polymerizable phosphonate monomers, which can include without limitation vinyl phosphonic acid and vinyl diphosphonic acid, isopropenyl phosphonic acid, isopropenylphosphonic anhydride, (meth) allylphosphonic acid, ethylidene diphosphonic acid, vinylbenzylphosphonic acid, 2-(meth)-acrylamido-2-methylpropyl phosphonic acid, 3-(meth)acrylamido-2-hydroxypropylphosphonic acid, 2-methacrylamidoethylphosphonic acid, and 3-(meth)allyloxy-2-hydroxypropylphosphonic acid.

Sulfonic Containing Moieties

In one embodiment, a sulfonic containing moiety can be incorporated in the polymer by water-soluble sulfonic acid monomers, which can include but are not limited to one or more of 2-acrylamido-2-methyl propane sulfonic acid ('AMPS'), vinyl sulfonic acid, sodium (meth)allyl sulfonate, sulfonated styrene, (meth)allyloxybenzene sulfonic acid, sodium 1-(meth)allyloxy 2-hydroxy propyl sulfonate, salts of any of the foregoing, and mixtures of any of the foregoing. In an embodiment, the sulfonic containing moiety can be incorporated in the polymer after polymerization. Examples of this type of sulfonic containing moiety are sulfomethyl(meth)acrylamide and sulfoethyl(meth)acrylamide. For example, when the polymer contains (meth)acrylamide, the (meth)acrylamide moiety of the polymer can react with formaldehyde and sodium bisulfite to form sulfomethyl(meth)acrylamide. In one embodiment, the amount of sulfonic containing moiety is no greater than 40 mole percent of the polymer, or no greater than 30 mole percent of the polymer, or no greater than 20 mole percent of the polymer or may not be present.

Optional Nonionic Monomers

For purposes of this application, a nonionic monomer is defined as a monomer that is not capable of developing a charge in water at any pH range.

Optional non-ionic monomers can include $C_1$-$C_6$ alkyl esters of (meth)acrylic acid; (meth)acrylamide and the $C_1$-$C_8$ alkyl-substituted (meth)acrylamides; N-alkanol-substituted (meth)acrylamides such as N-methylol(meth)acrylamide; hydroxyl alkyl (meth)acrylates; hydroxyl alkyl (meth)acrylamides; isobutylene; styrene; (meth)acrylonitrile; vinyl acetate; and $C_1$-$C_6$ alkyl diesters of unsaturated vinylic acids, such as the $C_1$-$C_6$ alkyl diesters of maleic acid and itaconic acid. Examples of $C_1$-$C_6$ alkyl esters of (meth) acrylic acid include without limitation methyl methacrylate, methyl acrylate, ethyl acrylate, n-butyl acrylate, n-butyl methacrylate, t-butyl acrylate and t-butyl methacrylate. Examples of $C_1$-$C_8$ alkyl-substituted (meth)acrylamides include without limitation N,N-dimethyl acrylamide, t-butyl acrylamide, and t-octyl acrylamide. Examples of hydroxy alkyl (meth)acrylates include hydroxyethyl (meth)acrylate and hydroxypropyl (meth)acrylate. Nonionic monomers also include but are not limited to, vinyl alcohol typically derived from the hydrolysis of already polymerized vinyl acetate groups; 1-vinyl-2-pyrrolidone; vinyl lactam; allyl glycidyl ether; (meth)allyl alcohol; (meth) allyl alcohol polyethyleneglycol, ethylene glycol (meth) allyl ether, glycerol (meth)acrylate and others. In one embodiment the nonionic monomers are selected from the group consisting of methyl methacrylate, n-butyl acrylate, t-butyl acrylate, hydroxyethyl (meth)acrylate, hydroxypropyl (meth)acrylate, t-butyl acrylamide, acrylamide and N,N-dimethylacrylamide.

The optional nonionic monomers include water soluble non-ionic monomers and low water solubility non-ionic monomers.

As used herein with respect to water soluble non-ionic monomers, water soluble means that the monomer has a water solubility of at least 6 grams per 100 mls of water at 25° C., and low water solubility means that the monomer has a water solubility of less than 6 g per 100 mls at 25° C., preferably less than 3 g per 100 mls at 25° C.

Examples of water soluble non-ionic monomers include but are not limited to (meth)acrylamide, N,N-dimethylacrylamide, acrylonitrile, hydroxy $C_1$-$C_4$ alkyl (meth)acrylates such as hydroxyethyl (meth)acrylate and hydroxypropyl (meth)acrylate, vinyl alcohol typically derived from the hydrolysis of already polymerized vinyl acetate groups, 1-vinyl-2-pyrrolidone, vinyl lactam, allyl glycidyl ether, (meth)allyl alcohol, (meth) allyl alcohol polyethyleneglycol, ethylene glycol (meth) allyl ether, methoxy polyethylene glycol (meth) acrylate, polyethylene glycol (meth) acrylate, and others.

Examples of low water solubility nonionic monomers include but are not limited to $C_1$-$C_{18}$ alkyl esters, $C_2$-$C_{18}$ alkyl-substituted (meth)acrylamides, aromatic monomers, alpha-olefins, $C_1$-$C_6$ alkyl diesters of maleic acid and itaconic acid, vinyl acetate, glycidyl methacrylate, methacrylonitrile and others. $C_1$-$C_{18}$ alkyl esters of (meth)acrylic acid include but are not limited to methyl methacrylate, methyl acrylate, ethyl acrylate, n-butyl acrylate, n-butyl methacrylate, t-butyl acrylate and t-butyl methacrylate, 2-ethyl hexyl (meth)acrylates, lauryl (meth)acrylate, stearyl (meth)acrylate and others. $C_2$-$C_{18}$ alkyl-substituted (meth)acrylamides include but are not limited to such as N,N-diethyl acrylamide, t-butyl acrylamide, and t-octyl acrylamide, and others. The preferred optional nonionic low water solubility nonionic monomers are methyl (meth)acrylate, vinyl acetate and t-butyl acrylamide, with t-butyl acrylamide being particularly preferred.

In one embodiment low water solubility optional nonionic monomers are preferred.

In one embodiment, the amount of water soluble optional nonionic monomer is no greater than 40 mole percent of the polymer, or no greater than 25 mole percent of the polymer, or no greater than 10 mole percent of the polymer, or may not be present.

In one embodiment, the amount of low water solubility optional nonionic monomer is no greater than 50 mole percent of the polymer, or no greater than 20 mole percent of the polymer, or no greater than 15 mole percent of the polymer, or no greater than 10 mole percent of the polymer, or may not be present.

In a preferred embodiment, the polymer comprises a carboxylic acid monomer; a sulfonated pyrene monomer; phosphino groups; and a low water solubility optional nonionic monomer.

Polyether moieties can contribute to scale inhibition by a steric stabilization mechanism when present in the polymer either in the polymer backbone or as pendant groups. Scale inhibition by a steric stabilization mechanism is, however, typically more expensive and less economically feasible than scale inhibition by an electrostatic mechanism as is achieved with the water soluble polymers of the method of this disclosure. In one embodiment, the water treatment polymers of the method disclosed herein are substantially free of polyether moieties. Substantially free means that the polymer contains less than 10 mole percent polyether moieties, or less than 5 mole percent polyether moieties, or less than 1 mole percent polyether moieties, or is free of polyether moieties.

Polymerization

The polymerization of the fluorescent water treatment polymer is carried out in an appropriate solvent under standard polymerization conditions in the presence of an initiator, as is known in the art. In one aspect the reaction solvent can be water or a mixture of water and an alcohol such as isopropanol. The resulting polymer solution can be neutralized to a desired pH with an appropriate base. The neutralization can occur before, during or after polymerization or a combination thereof.

The polymer compositions are preferably prepared from a polymerization mixture in an aqueous medium in the presence of any initiator or initiating system capable of liberating free radicals under the reaction conditions employed. The free radical initiators are present in an amount ranging from about 0.01% to about 3% by weight based on total monomer weight. In an embodiment, the initiating system is soluble in water to at least 0.1 weight percent at 25° C. Suitable initiators include, but are not limited to, peroxides, azo initiators as well as redox systems, such as erythorbic acid, and metal ion based initiating systems. Initiators may also include both inorganic and organic peroxides, such as hydrogen peroxide, benzoyl peroxide, acetyl peroxide, and lauryl peroxide; organic hydroperoxides, such as cumene hydroperoxide and t-butyl hydroperoxide. In an embodiment, the inorganic peroxides, such as sodium persulfate, potassium persulfate and ammonium persulfate, are preferred. In another embodiment, the initiators comprise metal ion based initiating systems including Fe and hydrogen peroxide, as well as Fe in combination with other peroxides. Organic peracids such as peracetic acid can be used. Peroxides and peracids can optionally be activated with reducing agents, such as sodium bisulfite, sodium formaldehyde, or ascorbic acid, transition metals, hydrazine, and the like. The initiating system can be persulfate alone such as sodium or ammonium persulfate or a redox system with iron and persulfate with hydrogen peroxide. Azo initiators, especially water soluble azo initiators, may also be used. Water soluble azo initiators include, but are not limited to, 2,2'-Azobis[2-(2-imidazolin-2-yl)propane]dihydrochloride, 2,2'-Azobis[2-(2-imidazolin-2-yl)propane]disulfate dihydrate, 2,2'-Azobis(2-methylpropionamidine)dihydrochloride, 2,2'-Azobis[N-(2-carboxyethyl)-2-methylpropionamidine]hydrate, 2,2'-Azobis{2-[1-(2-hydroxyethyl)-2-imidazolin-2-yl]propane}dihydrochloride, 2,2'-Azobis[2-(2-imidazolin-2-yl)propane], 2,2'-Azobis(1-imino-1-pyrrolidino-2-ethylpropane)dihydrochloride, 2,2'-Azobis{2-methyl-N-[1,1-bis(hydroxymethyl)-2-hydroxyethyl]propionamide}, 2,2'-Azobis[2-methyl-N-(2-hydroxyethyl)propionamide] and others.

The molecular weight of the polymers may be controlled by various compounds used in the art including for example chain transfer agents such as mercaptans, ferric and cupric salts, bisulfites, and lower secondary alcohols, preferably isopropanol. The preferred weight average molecular weight is less than 50000, preferably less than 30000 and most preferably less than 20000. The preferred weight average molecular weight is greater than 1000, more preferably greater than 2000 and most preferably greater than 3000.

Neutralization

One skilled in the art will recognize that the carboxylic acid monomers are typically partially or completely neutralized before or during polymerization to increase reactivity of the monomers and improve their incorporation into the polymer. The polymers may be supplied as the acid or partially neutralized. This allows the water treatment formulator to formulate these polymers in low pH acidic formulations and high pH alkaline formulations.

Suitable neutralization agents include but are not limited to alkali or alkaline earth metal hydroxides, or amines. Neutralization agents can be sodium, potassium or ammonium hydroxides or mixtures thereof. Amines include but are not limited to ethanol amine, diethanolamine, triethanolamine and others.

Corrosion Inhibitors

Water treatment formulations may contain other ingredients such as corrosion inhibitors. These corrosion inhibitors can inhibit corrosion of copper, steel, aluminum, or other metals that may be present in the water treatment system. Azoles are typically used in these water treatment formulations as copper corrosion inhibitors. The benzotriazole is typically formulated in acidic formulations. The tolyl triazole is formulated in alkaline formulations. If a corrosion inhibitor is used, the formulator will choose a pH range suitable for the selected corrosion inhibitor, to achieve the desired solubility of these azoles, in the selected pH ranges. One skilled in the art will recognize that other azoles or non azole-containing copper corrosion inhibitors may be used in combination with these polymers. In addition, corrosion inhibitors that inhibit corrosion of other metals also can be used.

Water Treatment Formulations and Methods of Use

In accordance with the method herein, the polymer compositions may be dosed directly to the aqueous systems or may be formulated into various water treatment formulations which may then be dosed to the aqueous systems.

The fluorescent emissions of the dosed water system are then monitored. Such monitoring can be accomplished using known techniques as disclosed, for example, in U.S. Pat. Nos. 5,171,450, 5,986,030, and 6,280,635. Fluorescent monitoring such as in-line monitoring allows the user to monitor the amount of water treatment polymer used to mitigate carbonate scale in the aqueous system. This is especially useful in stressed systems where calcium and/or magnesium carbonate scaling is problematic.

A stressed system, as used herein means a system having a Langelier Saturation Index of at least 2.0. The Langelier Saturation Index or LSI is a common method used to predict the potential for calcium and/or magnesium carbonate precipitation in water. This index is based on the difference between the actual pH of the water in question and the saturation pH of calcium and/or magnesium carbonate, at the current conditions of the water (actual pH−saturation pH=LSI factor). As a result, an LSI factor of zero indicates that the water is at equilibrium. LSI factors greater than zero indicate that the water is supersaturated and will precipitate calcium and/or magnesium carbonate without some form of treatment. The greater the LSI, the greater the driving force for precipitation and scaling. Many factors can contribute to increasing LSI. Increasing pH values has a direct effect on increasing LSI. Increasing calcium and/or magnesium and alkalinity concentrations, increasing temperatures, and increasing conductivity all indirectly increase LSI factors by lowering the saturation pH of the water in question. LSI factors of greater than 2.0 are generally considered stressful conditions in the field, with factors from 2.5 to 3.0 considered extremely high stress. Minimizing the amount of orthophosphate requires the use of higher pH to minimize corrosion which leads to more highly stressed systems. Therefore, it is advantageous to have a low orthophosphate or no orthophosphate treatment system. For purposes of this disclosure, a low orthophosphate system means less than 10 ppm orthophosphate, more preferably less than 8 ppm orthophosphate and most preferably less than 6 ppm orthophosphate. A no orthophosphate system means that the orthophosphate is less than 1 ppm or preferably 0 ppm. Note that the orthophosphate that may be present in the water system as referred to above is distinct from the phosphino group moieties and the optional phosphono group moieties and pendant phosphonate group moieties of the water-soluble fluorescent water treatment polymers of the disclosure.

The water treatment polymers as disclosed herein are effective in both non-stressed water systems and in stressed water systems having an LSI value of 2 or greater. In one aspect, use of the fluorescent water treatment polymers disclosed will achieve carbonate inhibition of at least 80% when the fluorescent water treatment polymer is dosed to a system having an LSI of 2 at an initial treatment rate of no greater than 100 ppm, in one embodiment at an initial treatment rate of no greater than 50 ppm, in one embodiment at an initial treatment rate of no greater than 25 ppm, in one embodiment at an initial treatment rate of no greater than 20 ppm, in one embodiment at an initial treatment rate of no greater than 10 ppm, in one embodiment at an initial treatment rate of no greater than 5 ppm, wherein all polymer concentrations are stated with respect to the amount of active polymer, and wherein carbonate inhibition is measured using the test protocol described in Example 8. In certain non-stressed aqueous systems where large volumes of water are continuously treated to maintain low levels of deposited matter, the polymers may be used at levels as low as 0.5 ppm. The upper and lower limits of the level of polymer used will be dependent upon the particular aqueous system to be treated. Accurately monitoring the amount of polymer in the water system by measuring the fluorescent emission allows for use of the minimum amount of polymer. This has both a favorable economic and environmental impact.

One skilled in the art will recognize that the fluorescent water treatment polymers of the disclosed method can be used in formulations containing inert tracers. These tracers include but are not limited to, 2-naphthalene sulfonic acid, rhodamine, Fluorescein and 1,3,6,8-Pyrenetetrasulfonic acid, tetrasodium salt (PTSA). This allows for complete monitoring of the system as described in U.S. Pat. Nos. 5,171,450 and 6,280,635.

EXAMPLES

Example 1: Synthesis of Polymer

An initial charge of 108.6 g of deionized water was added to a 1-liter glass reactor with inlet ports for an agitator, water cooled condenser, thermocouple, and adapters for the addition of monomer and initiator solutions. The reactor contents were heated to 95° C. A mixed monomer solution which consisted of 170.52 g of acrylic acid (2.37 moles, 95.2 mole percent of polymer), 0.83 g of methallyl oxy pyranine (formula weight 578.3, 0.0014 moles, 0.058 mole percent of polymer) dissolved in a mixture of 0.83 g of 1-propanol, and 2.5 g of water was mixed and then fed to the reactor via measured slow-addition with stirring over a period of 4 hours. A solution of 13.8 g of sodium hypophosphite monohydrate (0.119 moles, 4.78 mole percent of polymer) dissolved in 41.2 g of water was concurrently fed into the reactor over 4 hours starting at the same time as the monomer solution. An initiator solution of 3.8 grams of sodium persulfate dissolved in 39 grams water was concurrently added, starting at the same time as the monomer solution, for a period of 4 hours and 15 minutes. The reaction product was then held at 95° C. for 60 minutes. The polymer solution was cooled and then neutralized with 23 g of 50% sodium hydroxide. The final polymer solution had a solids content of about 45.8%, and a pH of 4.0.

Example 2

An initial charge of 190.1 g of deionized water was added to a 1-liter glass reactor with inlet ports for an agitator, water cooled condenser, thermocouple, and adapters for the addition of monomer and initiator solutions. The reactor contents were heated to 95° C. A mixed monomer solution which consisted of 298.5 g of acrylic acid (94.4 mole %), 24.1 g of sodium hypophosphite monohydrate (5.3 mole %) 7.25 g of methallyl oxy pyranine (0.285 mole % of the polymer) dissolved in a mixture of 7.25 g of 1-propanol, and 102.5 of water was mixed and then fed to the reactor via measured slow-addition with stirring over a period of 4 hours. An initiator solution of 6.7 grams of sodium persulfate dissolved in 68.4 grams water was concurrently added, starting at the same time as the monomer solution, for a period of 4 hours and 25 minutes. The reaction product was then held at 95° C. for 60 minutes. The polymer solution was cooled and then neutralized with 40.1 g of 50% sodium hydroxide solution. The final polymer solution had a solids content of about 46.4% and a pH of 3.9.

Example 3

An initial charge of 214 g of deionized water was added to a 1-liter glass reactor with inlet ports for an agitator, water cooled condenser, thermocouple, and adapters for the addition of monomer and initiator solutions. The reactor contents were heated to 100° C. A mixed monomer solution which consisted of 325.1 g of acrylic acid (86 mole %), 29.1 g of sodium hypophosphite monohydrate (5.3 mole %), 207.3 g of 50% solution of sodium 2-acrylamido-2-methyl propane sulfonate (8.6 mole %), 1.58 g of methallyl oxy pyranine (0.052 mole % of the polymer) dissolved in a mixture of 1.5 g of 1-propanol, and 72 g of water was mixed and then fed to the reactor via measured slow-addition with stirring over a period of 2 hours. An initiator solution of 7.9 grams of sodium persulfate dissolved in 61 grams water was concurrently added, starting at the same time as the monomer solution, for a period of 2 hours and 15 minutes. The reaction product was then held at 100° C. for 120 minutes. The final polymer solution had a solids content of about 50.6% and a pH of 2.6.

Example 4: Synthesis of Polymer (Comparative)

An initial charge of 137 g deionized water and 200.5 g of maleic anhydride (2.04 moles, 99.94 mole percent), 0.05 g of ferrous ammonium sulfate hexahydrate was added to a 2-liter glass reactor with inlet ports for an agitator, water cooled condenser, thermocouple, and adapters for the addition of monomer and initiator solutions. The reactor contents were heated, 95° C. A monomer solution which consisted of 0.6 g of methallyl oxy pyranine (0.001 moles, 0.05 mole percent) dissolved in 0.6 g of 1-propanol, and 52 g of water was fed to the reactor via measured slow-addition with stirring over a period of 6 hours. An initiator solution of 155.8 g of 35% hydrogen peroxide, dissolved in 550 grams water was concurrently added, starting at the same time as the monomer solution, for a period of 6 hours. The reaction product was then held at 95° C. for 60 minutes. The final reaction mixture was a dark amber colored solution with solids of about 40%.

Example 5: Synthesis of Polymer (Comparative)

An initial charge of 137 g deionized water and 200.5 g of maleic anhydride (2.05 moles, 90.82 mole percent), 0.05 g of ferrous ammonium sulfate hexahydrate was added to a 2-liter glass reactor with inlet ports for an agitator, water cooled condenser, thermocouple, and adapters for the addition of monomer and initiator solutions. The reactor contents were heated, 95° C. A monomer solution which consisted of 0.6 g of methallyl oxy pyranine (0.001 moles, 0.046 mole percent) dissolved in 0.6 g of 1-propanol, and 72 g of water 21.4 g of styrene (0.2 moles, 9.1 mole percent) in 156 grams of isopropanol was fed to the reactor via measured slow-addition with stirring over a period of 6 hours. An initiator solution of 155.8 g of 35% hydrogen peroxide, dissolved in 550 grams water was concurrently added, starting at the same time as the monomer solution, for a period of 6 hours. The reaction product was then held at 95° C. for 60 minutes. The final polymer solution had a solids content of 40.3%.

Example 6: Synthesis of Polymer (Comparative)

An initial charge of 267.3 g of deionized water was added to a 1-liter glass reactor with inlet ports for an agitator, water cooled condenser, thermocouple, and adapters for the addition of monomer and initiator solutions. The reactor contents were heated to 95° C. A mixed monomer solution which consisted of 343.1 g of acrylic acid (99.95 mol %), 1.5 g of methallyl oxy pyranine (0.05 mole percent) dissolved in a mixture of 1.5 g of 1-propanol, and 37 g of water was mixed and then fed to the reactor via measured slow-addition with stirring over a period of 4 hours. An initiator solution of 15.3 grams of sodium persulfate dissolved in 78.2 grams water was concurrently added, starting at the same time as the monomer solution, for a period of 4 hours and 15 minutes. The reaction product was then held at 95° C. for 60 minutes. The polymer solution was cooled and then neutralized with 46 g of 50% sodium hydroxide. The final polymer solution had a solids content of about 47.4%, and a pH of 3.6.

The composition of the polymers of Examples 1-6 is summarized in Table 1.

TABLE 1

| Example No. | solvent | Monomer/molecule | Grams | moles | Mole % |
| --- | --- | --- | --- | --- | --- |
| 1 | water | Acrylic acid | 170.52 | 2.37 | 95.2 |
|   |   | methallyl oxy pyranine | 0.83 | 0.0014 | 0.058 |
|   |   | sodium hypophosphite monohydrate | 13.8 | 0.119 | 4.78 |

TABLE 1-continued

| Example No. | solvent | Monomer/ molecule | Grams | moles | Mole % |
|---|---|---|---|---|---|
| 2 | Water/IPA | Acrylic acid | 298.5 | | 94.4 |
| | | sodium hypophosphite monohydrate | 24.1 | | 5.3 |
| | | methallyl oxy pyranine | 7.25 | | 0.285 |
| 3 | Water/IPA | | | | |
| | | Acrylic acid | 325.1 | | 86 |
| | | sodium hypophosphite monohydrate | 29.1 | | 5.3 |
| | | AMPS Na (50%) | 207.3 | | 8.6 |
| | | methallyl oxy pyranine | 1.58 | | 0.052 |
| 4 (comparative) | water | Maleic | 200.5 | 2.04 | 99.94 |
| | | methallyl oxy pyranine | 0.6 | 0.001 | 0.05 |
| 5 (comparative) | Water/IPA | Maleic | 200.5 | 2.05 | 90.82 |
| | | methallyl oxy pyranine | 0.6 | 0.001 | 0.05 |
| | | Styrene | 21.4 | 0.2 | 9.1 |
| 6 (comparative) | | | | | |
| | | Acrylic acid | 343.1 | | 99.05 |
| | | methallyl oxy pyranine | 1.5 | | 0.05 |

Example 7—Fluorescence Measurements

Samples of the polymers from Examples 1, 4, and 5 each were diluted in water to 10 ppm and the fluorescent signal was determined by excitation of the sample at the excitation wavelengths and measurement at the emission wavelengths using a PerkinElmer LS 55 instrument as stated in Table 2, where the absorption and emission wavelengths are selected where the emitted fluorescence signal is the highest, and where "AA" is acrylic acid, maleic means maleic acid, and "tag" indicates the fluorescent monomer, methallyl oxy pyranine. Samples of the polymers from Examples 1, 2, and 6 each were diluted in water to 10 ppm and the pH adjusted to 9 and the fluorescent signal was determined by excitation of the sample at the excitation wavelengths and measurement at the emission wavelengths using a Shimadzu RF 6000 instrument as stated in Table 2, where the absorption and emission wavelengths are selected where the emitted fluorescence signal is the highest.

TABLE 2

Fluorescence data for polymers

| Polymer | Composition (with mole percent of each component) | Instrument | Excitation wavelength nm | Emission wavelength nm | fluorescence signal/ppm polymer |
|---|---|---|---|---|---|
| Example 1 | AA/phosphino/tag 95.2/4.78/0.058 | PerkinElmer LS 55 | 377 | 433 | 162.1 |
| Example 4 (Comparative) | Maleic/tag 99.94/0.05 | PerkinElmer LS 55 | 377 | 432 | 8.22 |
| Example 5 (Comparative) | Maleic/styrene/tag 90.8/9.1/0.046 | PerkinElmer LS 55 | 377 | 432 | 8 |
| Example 1 (at pH = 9) | AA/phosphino/tag 95.2/4.78/0.058 | Shimadzu RF 6000 | 407 | 437 | 427.3 |
| Example 2 (at pH = 9) | AA/phosphino/tag 94.4/5.3/0.285 | Shimadzu RF 6000 | 408 | 435 | 1768.9 |
| Example 6 (Comparative) (at pH = 9) | AA/tag 99.95/0.05 | Shimadzu RF 6000 | 371 | 424 | 90.4 |

These data indicate that Example 1 containing the phosphino group had an unexpectedly superior fluorescent signal, at both acidic and alkaline pH, while the polymers containing maleic component in the 90-100 mole percent range (Comparative Examples 4 and 5) exhibit suppressed fluorescent signal. These data indicate that Example 1 containing the phosphino group had an unexpectedly superior fluorescent signal, at pH 9, while the polymer containing just acrylic acid (Comparative Example 6) exhibited a lower fluorescent signal.

Example 8—Carbonate Inhibition

Various polymers were evaluated for their ability to prevent the precipitation of calcium carbonate in typical cooling water conditions, a property commonly referred to as the threshold inhibition. Solutions were prepared in which the weight ratio of calcium concentration to alkalinity was 1.000:1.448 to simulate typical conditions in industrial water systems used for cooling. Generally, water wherein the alkalinity is proportionately less will be able to reach higher levels of calcium, and water containing a proportionally greater amount of alkalinity will reach lower levels of calcium. Since cycle of concentration is a general term, one cycle was chosen, in this case, to be that level at which calcium concentrations equaled 100.0 mg/L Ca as $CaCO_3$ (40.0 mg/L as Ca). The complete water conditions at one cycle of concentration (i.e., make-up water conditions) were as follows:

Simulated Make-Up Water Conditions:
  100.00 mg/L Ca as $CaCO_3$ (40.0 mg/L as Ca) (one cycle of concentration)
  49.20 mg/L Mg as $CaCO_3$ (12.0 mg/L as Mg)
  2.88 mg/L Li as $CaCO_3$ (0.4 mg/L as Li)
  144.80 M Alkalinity (144.0 mg/L as $HCO_3$)
  13.40 P Alkalinity (16.0 mg/L as $CO_3$)
Materials:
  One incubator/shaker, containing a 125 mL flask platform, with 34 flask capacity
  Screw-cap Erlenmeyer Flasks (125 mL)
  Deionized Water
  Analytical balance
  Electronic pipette(s) capable of dispensing between 0.0 mL and 2.5 mL
  250 Cycle Hardness Solution*

10,000 mg/L treatment solutions, prepared using known active solids of the desired treatment*
10% and 50% solutions of NaOH
250 Cycle Alkalinity Solution*
0.2 μm syringe filters or 0.2 μm filter membranes
Volumetric Flasks (100 mL)
Concentrated Nitric Acid

*See solution preparations in next section.

Solution Preparations:

All chemicals used were reagent grade and weighed on an analytical balance to ±0.0005 g of the indicated value. All solutions were made within thirty days of testing. The hardness and alkalinity solutions were prepared in a one liter volumetric flask using DI water. The following amounts of chemical were used to prepare these solutions—

250 Cycle Hardness Solution:
 10,000 mg/L Ca⇒36.6838 g $CaCl_2 \cdot 2H_2O$
 3,000 mg/L Mg⇒25.0836 g $MgCl_2 \cdot 6H_2O$
 100 mg/L Li⇒0.6127 g LiCl 250 Cycle Alkalinity Solution:
 36,000 mg/L $HCO_3$⇒48.9863 g $NaHCO_3$
 4,000 mg/L $CO_3$⇒7.0659 g $Na_2CO_3$ 10,000 mg/L Treatment Solutions:

Using percentage of active product in the supplied treatment, 250 mL of a 10,000 mg/L active treatment solution was made up for every treatment tested. The pH of the solutions was adjusted to between 8.70 and 8.90 using 50% and 10% NaOH solutions by adding the weighed polymer into a specimen cup or beaker and filling with DI water to approximately 90 mL. The pH of this solution was then adjusted to approximately 8.70 by first adding the 50% NaOH solution until the pH reached 8.00, and then by using the 10% NaOH until the pH equaled 8.70. The solution was then poured into a 250 mL volumetric flask. The specimen cup or beaker was rinsed with DI water and this water was added to the flask until the final 250 mL was reached. The amount of treatment product to be weighed was calculated as follows:

$$\text{Grams of treatment needed} = \frac{(10{,}000 \text{ mg/L})(0.25 \text{ L})}{(\text{decimal \% of active treatment})}(1000 \text{ mg})$$

Test Setup Procedure:

The incubator shaker was turned on and set for a temperature of 50° C. to preheat. Screw cap flasks were set out in groups of three to allow for triplicate testing of each treatment, allowing for testing of different treatments. The one remaining flask was used as an untreated blank.

96.6 grams of DI water was weighed into each flask.

Using a 2.5 mL electric pipette, 1.20 mL of hardness solution was added to each flask to simulate four cycles of make-up water.

Using a 250 μL electronic pipette, 200 μL of desired treatment solution was added to each flask to achieve a 20 ppm active treatment dosage. A new tip on the electric pipette was used for each treatment solution so cross contamination did not occur.

Using a 2.5 mL electric pipette, 1.20 mL of alkalinity solution was added to each flask to simulate four cycles of make-up water having an LSI value of 2.79. The addition of alkalinity was done while swirling the flask, so as not to generate premature scale formation from high alkalinity concentration pooling at the addition site.

One "blank" solution was prepared in the exact same manner as the above treated solutions, except DI water was added in place of the treatment solution.

All 34 flasks uncapped were placed onto the shaker platform and the door closed. The shaker was run at 250 rpm and 50° C. for 17 hours.

A "total" solution was prepared in the exact same manner as the above treated solutions were prepared, except that DI water was used in place of both the treatment solution and alkalinity solution. This solution was capped and left overnight outside the shaker.

Test Analysis Procedure:

Once 17 hours had passed, the 34 flasks were removed from the shaker and allowed to cool for one hour. Each flask solution was filtered through a 0.2 μm filter membrane. 250 μl of nitric acid was added to 10 ml of each filtrate, and each filtrate was analyzed directly for lithium, calcium, and magnesium concentrations by an Inductively Coupled Plasma (ICP) Optical Emission System. The "total" solution was analyzed in the same manner.

Calculations of Results:

Once the lithium, calcium, and magnesium concentrations were known in all 34 shaker samples and in the "total" solution, the percent inhibition was calculated for each treatment. The lithium was used as a tracer of evaporation in each flask (typically about ten percent of the original volume). The lithium concentration found in the "total" solution was assumed to be the starting concentration in all 34 flasks. The concentrations of lithium in the 34 shaker samples were each divided by the lithium concentration found in the "total" sample. These results provided the multiplying factor for increases in concentration, due to evaporation. The calcium and magnesium concentrations found in the "total" solution were also assumed to be the starting concentrations in all 34 flasks. By multiplying these concentrations by each calculated evaporation factor for each shaker sample, the final intended calcium and magnesium concentration for each shaker sample was determined. By subtracting the calcium and magnesium concentrations of the "blank" from both the actual and intended concentrations of calcium and magnesium, then dividing the resulting actual concentration by the resulting intended concentration and multiplying by 100, the percent inhibition for each treated sample was calculated. The triplicate treatments were averaged to provide more accurate results.

TABLE 3

| | Carbonate inhibition at a LSI of 2.79 | | |
|---|---|---|---|
| Polymer | Composition (with mole percent of each component) | % Carbonate inhibition (4 ppm polymer) | % Carbonate inhibition (5 ppm polymer) |
| Example 1 | AA/phosphino/tag = 95.2/4.78/0.058 | 95 | 100 |
| Example 4 (Comparative) | Maleic/tag = 99.94/0.05 | 10 | 20 |

In the test above, anything above 80% inhibition is considered acceptable. These data in Table 3 indicate that the carbonate inhibition performance of the polymer of Example 1 is excellent, while the carbonate inhibition performance of comparative Example 4 would not be considered acceptable.

Example 9: Synthesis of Polymer

An initial charge of 206.4 g of deionized water was added to a 1-liter glass reactor with inlet ports for an agitator, water cooled condenser, thermocouple, and adapters for the addition of monomer and initiator solutions. The reactor contents were heated to 95° C. A mixed monomer solution which consisted of 324 g of acrylic acid (94.7 mole %), 26.2 g of sodium hypophosphite monohydrate (5.2 mole %) 3.2 g of methallyl oxy pyranine (0.1 mole percent of the polymer) dissolved in a mixture of 3.2 g of 1-propanol, and 84 of water was mixed and then fed to the reactor via measured slow-addition with stirring over a period of 4 hours. An initiator solution of 7.3 grams of sodium persulfate dissolved in 74 grams water was concurrently added, starting at the same time as the monomer solution, for a period of 4 hours and 15 minutes. The reaction product was then held at 95° C. for 60 minutes. The polymer solution was cooled and then neutralized with 68.3 g of 28% ammonium hydroxide solution. The final polymer solution had a solids content of about 46%.

Example 10: Phosphate Inhibition Testing

The performance of the polymers of the invention was measured for phosphate inhibition and iron inhibition, using the following method.

Solution "A" was prepared using sodium hydrogen phosphate and sodium tetraborate decahydrate, to create a solution containing 20 mg/L of phosphate, and 98 mg/L of borate and a pH of from 8.0-9.5.

Solution "B" was prepared calcium chloride dihydrate and ferrous ammonium sulfate, to create a solution containing 400 mg/L of calcium and 4 mg/L of iron at a pH of from 3.5-7.0.

The amount of polymer to add to solutions A and B was calculated to provide a 1.00 g/L (1000 mg/L) solids/active solution for testing. The calculations were based upon percent solids per sample in the following manner: % solids/100=X (decimal solids) and (1.000 g/L)/X=g/L polymer to yield a 1000 mg/L polymer solution.

Fifty (50) ml of Solution "B" was dispensed into a 125 ml Erlenmeyer flask using a Brinkman dispensette. Using a graduated pipette, the calculated amount of polymer solution was added to give the desired treatment level (i.e., 1 ml of 1000 mg/L polymer solution=10 mg/L in samples). Fifty (50) ml of Solution "A" was dispensed into the 125 ml Erlenmeyer flask using a Brinkman dispensette.

Using a Brinkman dispensette, at least three blanks (samples containing no polymer treatment) were prepared by dispensing 50 ml of Solution "B" and 50 ml of Solution "A" to a 125 ml Erlenmeyer flask. The flasks were stoppered and placed in a water bath set at 70° C.+/−5° C. for 16 to 24 hours.

All of the flasks were then removed from the water bath and allowed to cool to the touch. A vacuum apparatus was assembled using a 250 ml side-arm Erlenmeyer flask, vacuum pump, moisture trap, and Gelman filter holder. The samples from the 125 ml Erlenmeyer flask were filtered into the 250 ml side-arm Erlenmeyer flask using 0.2 micron filter paper. The filtrate from the 250 ml side-arm Erlenmeyer flask was transferred into a clean 100 ml specimen cup. The samples were evaluated for phosphate inhibition using a HACH DR/3000 Spectrophotometer following the procedure set forth in the operator's manual.

The samples were evaluated for iron inhibition using ICP (inductively coupled plasma) to quantify iron.

The % Phosphate inhibition for each treatment level was determined by calculating (S−B)/(T−B)*100, where S=mg/L phosphate in Sample, B=mg/L phosphate in Blank (sample with no treatment) and T=mg/L Total phosphate added.

The % iron inhibition for each treatment level was determined by calculating $(S_i-B_i)/(T_i-B_i)*100$, where $S_i$=mg/L iron in Sample, $B_i$=mg/L iron in Blank (sample with no treatment), and $T_i$=mg/L Total iron added.

Results of the analysis are in Table 4 below.

TABLE 4

The phosphate inhibition performance of polymer.

| Polymer | % phosphate inhibition at 20 ppm polymer | % iron inhibition at 20 ppm polymer |
|---|---|---|
| Example 3 | 95 | 94 |

The specific examples herein disclosed are to be considered as being primarily illustrative. Various changes beyond those described will, no doubt, occur to those skilled in the art; and such changes are to be understood as forming a part of this invention insofar as they fall within the spirit and scope of the appended claims.

What is claimed is:

1. A fluorescent water treatment polymer comprising
(i) at least one water soluble carboxylic acid monomer, other than maleic acid, present in an amount of 10-99.998 mol %;
(ii) at least one sulfonated pyrene-containing fluorescent monomer selected from

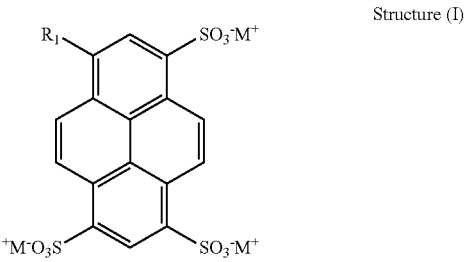

Structure (I)

wherein $R_1$ is selected from the group consisting of (meth)allyloxy, vinyl benzyloxy, (meth)acryl, (meth)acrylamidopropyl, 2-hydroxy-3-(meth)allyloxypropyl, (meth)acrylamido, 3-isopropenyl-α,α-dimethylbenzyl urethane, and (meth)allyl urethane,
and $M^+$ is independently selected from hydrogen, alkali metal, alkaline earth metal, and amine salt,
and

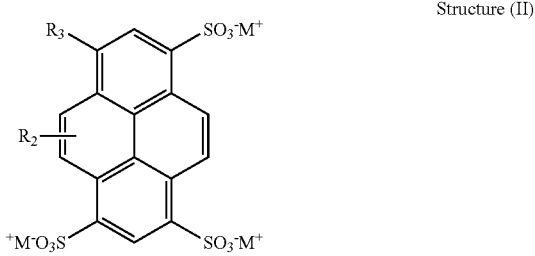

Structure (II)

wherein $R_2$ is selected from the group consisting of (meth)allyl, vinyl benzyl, (meth)acryl, (meth)acrylamidopropyl, and 2-hydroxy-3-(meth)allyloxypropyl, $R_3$ is selected from hydrogen, —OH, and —SO$_3^-$M$^+$, and M$^+$ is independently selected from hydrogen, alkali metal, alkaline earth metal, and amine salt, said sulfonated pyrene-containing fluorescent monomer being present in an amount of 0.001-5 mol %; and (iii) at least one phosphino group wherein the phosphorous atom of the phosphino group is in the polymer backbone, said phosphino group being present in an amount of 0.001-20 mol %.

2. The fluorescent water treatment of polymer of claim 1 wherein said water soluble carboxylic acid monomer other than maleic acid is selected from one or more of the group consisting of acrylic acid, methacrylic acid, itaconic acid, citraconic acid, mesaconic acid, glutaconic acid, aconitic acid, ethacrylic acid, alpha-chloro-acrylic acid, alpha-cyano acrylic acid, alpha-chloro-methacrylic acid, alpha-cyano methacrylic acid, beta methyl-acrylic acid (crotonic acid), beta-acryloxy propionic acid, sorbic acid, alpha-chloro sorbic acid, angelic acid, tiglic acid, p-chloro cinnamic acid, monomethyl maleate, monoethyl maleate, salts and anhydrides of any of the foregoing, and mixtures of any of the foregoing.

3. The fluorescent water treatment polymer of claim 1 wherein said phosphino moieties are obtained in the water treatment polymer backbone by polymerizing the water treatment polymer in a polymerization mixture comprising one or more molecules having the structure

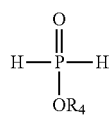

Structure (III)

where $R_4$ is selected from hydrogen, $C_1$-$C_4$ alkyl, phenyl, alkali metal, or an equivalent of an alkaline earth metal atom, an ammonium ion or an amine residue.

4. The fluorescent water treatment polymer of claim 1 further comprising maleic acid in an amount no greater than 75 mol %.

5. The fluorescent water treatment polymer of claim 1 further comprising a phosphorous containing group selected from phosphono groups and phosphate-containing monomers.

6. The fluorescent water treatment polymer of claim 1 further comprising a sulfonic containing moiety.

7. The fluorescent water treatment polymer of claim 6 wherein said sulfonic containing moiety is selected from one or more of 2-acrylamido-2-methyl propane sulfonic acid ('AMPS'), vinyl sulfonic acid, sodium (meth)allyl sulfonate, sulfonated styrene, (meth)allyloxybenzene sulfonic acid, sodium 1-(meth)allyloxy 2-hydroxy propyl sulfonate, sulfomethyl(meth)acrylamide, sulfoethyl(meth)acrylamide, salts of any of the foregoing, and mixtures of any of the foregoing.

8. The fluorescent water treatment polymer of claim 6 wherein said sulfonic containing moiety is present in the polymer at no greater than 20 mol %.

9. The fluorescent water treatment polymer of claim 1 further comprising one or more non-ionic monomers.

10. The fluorescent water treatment polymer of claim 9 wherein said one or more nonionic monomers is selected from one or more of the group consisting of $C_1$-$C_6$ alkyl esters of (meth)acrylic acid; (meth)acrylamide and the $C_1$-$C_8$ alkyl-substituted (meth)acrylamides; N-alkanol-substituted (meth)acrylamides; hydroxyl alkyl (meth)acrylates; hydroxyl alkyl (meth)acrylamides; isobutylene; styrene; (meth)acrylonitrile; vinyl acetate; $C_1$-$C_6$ alkyl diesters of unsaturated vinylic acids; vinyl alcohol; 1-vinyl-2-pyrrolidone; vinyl lactam; allyl glycidyl ether; (meth)allyl alcohol; and glycerol (meth)acrylate.

11. The fluorescent water treatment polymer of claim 9 wherein the non-ionic monomer is a water soluble non-ionic monomer selected from the group consisting of (meth)acrylamide, N,N-dimethylacrylamide, acrylonitrile, hydroxy $C_1$-$C_4$ alkyl (meth)acrylate, vinyl alcohol, 1-vinyl-2-pyrrolidone, vinyl lactam, allyl glycidyl ether, (meth)allyl alcohol, (meth) allyl alcohol polyethyleneglycol, ethylene glycol (meth) allyl ether, methoxy polyethylene glycol (meth)acrylate, and polyethylene glycol (meth) acrylate.

12. The fluorescent water treatment polymer of claim 9 wherein the non-ionic monomer is a low water solubility nonionic monomer selected from the group consisting of $C_1$-$C_{18}$ alkyl esters, $C_2$-$C_{18}$ alkyl-substituted (meth)acrylamides, aromatic monomers, alpha-olefins, $C_1$-$C_6$ alkyl diesters of maleic acid and itaconic acid, vinyl acetate, glycidyl methacrylate, and methacrylonitrile.

13. The fluorescent water treatment polymer of any of claim 12 wherein the low water solubility nonionic monomer comprises no greater than 50 mol % of the polymer.

14. A water treatment formulation comprising the fluorescent water treatment polymer of claim 1.

15. A method of controlling scale in an industrial water system comprising the steps of (a) dosing the industrial water system with the water treatment formulation of claim 14, and (b) monitoring fluorescent emissions of the industrial water system.

* * * * *